US007025961B1

(12) United States Patent
Narum et al.

(10) Patent No.: US 7,025,961 B1
(45) Date of Patent: Apr. 11, 2006

(54) ANTI-PLASMODIUM COMPOSITION AND METHODS OF USE

(75) Inventors: David L. Narum, Gaithersburg, MD (US); Kim Lee Sim, Gaithersburg, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/914,694

(22) PCT Filed: Mar. 3, 2000

(86) PCT No.: PCT/US00/05820

§ 371 (c)(1),
(2), (4) Date: Jan. 31, 2002

(87) PCT Pub. No.: WO00/52056

PCT Pub. Date: Sep. 8, 2000

Related U.S. Application Data (60) Provisional application No. 60/153,575, filed on Sep. 13, 1999, provisional application No. 60/122,842, filed on Mar. 4, 1999.

(51) Int. Cl.
*A61K 39/395* (2006.01)
*A61K 39/40* (2006.01)
*C07K 5/06* (2006.01)
*C12N 16/00* (2006.01)

(52) U.S. Cl. .................. 424/130.1; 424/139.1; 424/141.1; 424/151.1; 435/326; 435/332; 435/342; 530/387.1; 530/388.1; 530/388.2; 530/388.4; 530/388.6

(58) Field of Classification Search .......... 424/130.1, 424/139.1, 141.1, 151.1; 435/326, 332, 342; 530/387.1, 388.1, 388.2, 388.4, 388.6
See application file for complete search history.

(56) References Cited

U.S. PATENT DOCUMENTS 3,817,837 A   6/1974   Rubenstein et al.

FOREIGN PATENT DOCUMENTS

WO   WO 95/07353   3/1995
WO   WO 96/40766   12/1996

OTHER PUBLICATIONS

Ohas et al (Infection and Immunity vol. 72, No. 2, pp 735-741, 2004).*
Adams, J. H., Hudson, D. E., Torii, M., Ward, G. E., Wellems, T. E., Aikawa, M., Miller, L. H. "The Duffy receptor family of *Plasmodium knowlesi* is located within the mocronemes of invasive malaria merozoites." Cell. 63: 141-153, 1990.
Adams, J. H., Sim, B. K. L., Dolan, S. A., Fang, X., Kaslow, D. C., Miller, L. H. "A family of erythrocyte binding proteins of malaria parasites." Proc. Natl. Acad. Sci. 89: 7085-7089 (1992).
Chitnis, C. E., Miller, L. H. Identification of the erythrocyte binding domains of *Plasmodium vivax* and *Plasmodium knowlesi* proteins involved in erythrocyte invasion. J Exp Med Aug. 1, 1994; 180(2) :497-506.
Camus, D., and T. J. Hadley. A *Plasmodium falciparum* antigen that binds to host erythrocytes and merozoites. Science. 1985; 230, No. 4725:553.
Fang, X., Kaslow, D. C., Adams, J. H., Miller, L. H. "Cloning of the *Plasmodium vivax* Duffy receptor." Mol. Biochem. Parasitol. 44: 125-132 (1991).
Hadley, T. J., Erkmen, Z., Kaufman, B. M., Futrovsky, S., McGuinnis, M. H., Graves, P., Sadoff, J. C., Miller, L. H., Factors influencing invasion of erythrocytes by *Plasmodium falciparum* parasites: the effects of an N-acetyl glucosamine neoglycoprotein and an anti-glycophorin antibody. Am J Trop Med Hyg Sep. 1986; 35(5) :898-905.

(Continued)

*Primary Examiner*—Mark Navarro
(74) *Attorney, Agent, or Firm*—Knobbe, Martens, Olson & Bear, LLP (57) ABSTRACT

Compositions that inhibit the binding of *Plasmodium falciparum* to erythrocytes are provided. More particularly, antibodies specific for *Plasmodium falciparum* binding proteins and blocking peptides that prevent the binding of *Plasmodium falciparum* are included in the present invention. The methods provided utilize the antibody and peptide compositions provided herein and include methods for the diagnosis, prevention, and treatment of *Plasmodium falciparum* diseases such as malaria as well as methods for the detection of *Plasmodium falciparum* in biological samples and culture media.

8 Claims, 3 Drawing Sheets

OTHER PUBLICATIONS

Miller, L. H., Mason, S. J., Dvorak, J. A., McGinniss, M. H., Rothman, I. K., Erythrocyte receptors for (*Plasmodium knowlesi*) malaria: Duffy blood group determinants. Science Aug. 15, 1975; 189-(4202) :531-3.

Orlandi, P. A., Klotz, F. W., and Haynes, J. D. "A malaria invasion receptor, the 175-kilodalton erythrocyte binding antigen of *Plasmodium falciparum* recognizes the terminal neu5Ac((2-3) gal-sequences of glycophorin A." J. Cell Biol. 116:901-909 (1992).

Sim, B. K., Orlandi, P. A., Haynes, J. D., Klotz, F. W., Carter J. M., Camus, D., Zegans, M. E., and Chulay, J. D. Primary structure of the 175K *Plasmodium falciparum* reythrocyte binding antigen and identification of a peptide which elicits antibodies that inhibit malaria merozoite invasion. J Cell Biol. 1990; 111, No. 5 Pt 1:1877-1884.

Sim, B. K. L., Chitnis, C. E., Wasniowska, K., Hadley, Y. J., Miller, L. H., Receptor and ligand domains for invasion of erythrocytes by *Plasmodium falciparum*. Science. 264: 1941-1944. (1994).

Sim, B. K. L., "Delineation of functional regions on *Plasmodium falciparum* EBA-175 by antibodies eluted from immune complexes." Molecular and Biochemical Parasitology, vol. 95 (1998) pp. 183-192.

Narum, D. L. et al. "Inhibition of *Plasmodium falciparum* sialic acid-dependent (alternative pathway) invasion mediated by antibodies against EBA-175 region II." American Journal of Tropical Medicine and Hygiene, vol. 61, No. 3 Suppl., (1999) pp. 205-206.

Luu, T. et al. "Epitope mapping of monoclonal antibodies that block the binding of the *Plasmodium falciparum* merozoite ligant EBA-175." American Journal of Tropical Medicine and Hygiene, vol. 61, No. 3 Suppl., (1999), pp. 492-493.

Hadley, T.J., "Invasion of erythrocytes by malaria parasites: a cellular and molecular overview." Annu Rev. Microbiol. (1986);40:451-77.

* cited by examiner

FIG. 1

|  |  |  | | | | | | | | Frequency |
|---|---|---|---|---|---|---|---|---|---|---|
| | | 344 | | | | | 353 | | | |
| EBA-175 RII | | C | V | P | P | R | R | Q E L C | | |
| | | | | | | | | | | |
| PEP R256-1 | C | N | M | V | P | M | S | R C | | 1/11 |
| | | | | | | | | | | |
| PEP R256-2 | C | W | S | I | N | P | R | W C | | 6/11 |

FIG. 2

Malaria: EBA-175 Neutralizing MABS

**Anti-RII mAbs neutralize merozoite invasion *in vitro***

| Strains | % Growth Inhibition (merozoite blockade) | | | |
|---|---|---|---|---|
| | mAb R216 | mAb R215 | mAb R217 | mAb R256 |
| FVO | 7<br>p=0.255 | 82<br>p=0.005 | 83<br>p=0.005 | 76<br>p=0.005 |
| 3D7 | 27<br>p=0.007 | 35<br>p=0.002 | 39<br>p=0.004 | 37<br>p=0.002 |

FIG. 3

SEQUENCE LISTING

<160> NUMBER OF SEQ ID NOS: 4

<210> SEQ ID NO 1
<211> LENGTH: 10
<212> TYPE: PRT
<213> ORGANISM: Plasmodium sp.

```
<400> SEQUENCE: 1

Cys Val Pro Pro Arg Arg Gln Glu Leu Cys
1               5                   10

<210> SEQ ID NO 2
<211> LENGTH: 9
<212> TYPE: PRT
<213> ORGANISM: Plasmodium sp.

<400> SEQUENCE: 2

Cys Asn Met Val Pro Met Ser Arg Cys
1               5

<210> SEQ ID NO 3
<211> LENGTH: 9
<212> TYPE: PRT
<213> ORGANISM: Plasmodium sp.

<400> SEQUENCE: 3

Cys Trp Ser Ile Asn Pro Arg Trp Cys
1               5

<210> SEQ ID NO 4
<211> LENGTH: 4
<212> TYPE: PRT
<213> ORGANISM: Plasmodium sp.

<400> SEQUENCE: 4

Gly Gly Gly Ser
1
```

ANTI-PLASMODIUM COMPOSITION AND METHODS OF USE

CROSS REFERENCE TO RELATED APPLICATIONS

This application represents the U.S. National Phase of International Application No. PCT/US00/05820 filed Mar. 3, 2000, designating the United States of America and published in English as WO 00/52056 on Sep. 8, 2000, which claims the benefit of priority of U.S. Provisional Application No. 60/153,575 filed Sep. 13, 1999, and U.S. Provisional Application No. 60/122,842 filed Mar. 4, 1999.

The U.S. Government has a paid-up license in this invention and the right in limited circumstances to require the patent owner to license others on reasonable terms as provided for by the terms of National Institutes of Health Grant No. R44 A136758.

FIELD OF THE INVENTION

The present invention relates to the fields of microbiology and immunology and more specifically relates to compositions and methods for the detection, diagnosis, and treatment of malaria. In particular, the invention pertains to peptides and antibodies that inhibit the binding of *Plasmodium falciparum* erythrocyte binding protein antigens to erythrocytes.

BACKGROUND OF THE INVENTION

Although endemic malaria has disappeared from the United States, malaria continues to be one of the most important infectious diseases in the world as it kills millions of people each year in countries throughout Africa, Asia and Latin America. The characteristic presentation of malaria is chills followed by a fever ranging from 104–107° F., followed by profuse sweating. Other manifestations of malaria include anemia decreased blood flow to vital central nervous system is involved, symptoms include delirium, convulsions, paralysis, coma, and even rapid death.

Malarial diseases in humans are caused by four species of the *Plasmodium* parasite: *P. falciparum, P. vivax*, P. ovali, and *P. malariae*. Each of these species is transmitted to the human via a female *Anopheles* mosquito that transmits *Plasmodium* parasites, or sporozoites. Once the sporozoites enter the bloodstream of the human, they localize in liver cells, or hepatocytes. One to two weeks later, the infected hepatocytes rupture and release mature parasites, or merozoites. The merozoites then begin the erythrocytic phase of malaria by attaching to and invading red blood cells, or erythrocytes.

The invasion of the erythrocytes by the malarial parasites is the direct cause of malarial pathogenesis and pathology. The fever, anemia, circulatory changes, and immunopathologic phenomena characteristic of malaria are largely the result of red cell rupture and the host's immune response to parasitized erythrocytes. For these reasons, the erythrocytic stage of the *Plasmodium* life cycle is of vital importance to vaccine development and treatment of malaria.

There are a number of strategies for developing new or novel therapeutics for the erythrocytic stage of malaria. One strategy is to identify parasitic molecules that are critical to the survival of the parasite. Extracellular merozoites released from infected hepatocytes or from infected erythrocytes must invade other erythrocytes within minutes if they are to survive. Invasion by the malaria parasite is dependent upon the binding of parasite proteins to receptors on the erythrocyte surface (Hadley et al., 1986).

Interestingly, different parasite species use different erythrocytic receptors for invasion of erythrocytes. *P. falciparum* invades erythrocytes through a 175 kDa erythrocyte binding protein called EBA-175. EBA-175 functions as an erythrocyte invasion ligand that binds to its receptor, glycophorin A, on erythrocytes during invasion (Camus and Hadley, 1985; Sim et al., 1990; Orlandi et al., 1992; Sim et al., 1994b). In contrast, the human *P. vivax* and the simian *P. knowlesi* invade erythrocytes by binding Duffy blood group antigens present on some erythrocytes (Miller et al., 1975). The genes encoding the Duffy antigen binding proteins of *P. vivax* and *P. knowlesi* have been cloned and sequenced (Fang et al., 1991 and Adams et al., 1990, respectively).

Sequencing of the genes encoding the proteins used by *P. vivax* and *P. knowlesi* for erythrocyte invasion demonstrated that these proteins are members of the same gene family as the genes that encode the EBA-175, the protein used by *P. falciparum* for erythrocyte invasion (Adams et al., 1992). Homology between the Duffy binding proteins and EBA-175 is restricted to 5' and 3' cysteine rich domains. Within these cysteine rich domains, the cysteines and some aromatic residues are conserved, but the intervening amino acid sequences differ. Sim et al. (1994b) demonstrated that the 5' cysteine rich domain of EBA-175 of *P. falciparum* contains the receptor binding domain, while Chitnis and Miller (1994) demonstrated that the 5' cysteine rich region of *P. vivax* and *P. knowlesi* contain the Duffy binding domain. See FIG. 1.

SUMMARY OF THE INVENTION

The present invention provides compositions and methods for detecting, diagnosing, and treating *Plasmodium* and *Plasmodium* related infections. In particular, the compositions include EBA-175 antibodies and peptides that specifically inhibit binding of *Plasmodium* erythrocyte binding proteins to erythrocytes. Preferably, the antibodies specifically bind to the EBA-175 erythrocyte binding protein of *P. falciparum*. In a further preferred embodiment, the antibodies are designated R215, R215, R217 and R256 and have the properties as described herein. Additionally, in another preferred embodiment, EBA-175 peptides have the amino acid sequences of SEQ ID NO:1, SEQ ID NO:2 and SEQ ID NO:3.

The EBA-175 antibodies of the present invention can be polyclonal antibodies or monoclonal antibodies. Antibodies specific for EBA-175 may be administered to a human or animal to passively immunize the human or animal against *P. falciparum* infection, thereby reducing *P. falciparum* related diseases such as malaria. EBA-175 peptides specific for *P. falciparum* erythrocyte binding proteins may be administered to a human or animal to immunize the human or animal against *P. falciparum* infection, thereby reducing *P. falciparum* related diseases such as malaria. The antibodies are also useful as in vitro research tools for studying malaria and for isolating large quantities of EBA-175 proteins. The EBA-175 antibodies can be used in diagnostic kits to detect the presence and quantity of *P. falciparum*, which is diagnostic or prognostic for the occurrence or recurrence of diseases such as malaria. Additionally, the EBA-175 peptides that inhibit binding of *P. falciparum* binding to erythrocytes can be used in diagnostic kits to detect the presence and quantity of *P. falciparum* antibodies, which is diagnostic or prognostic for the occurrence of diseases such as malaria.

The compositions also include *P. falciparum* antibodies and antibody fragments, *P. falciparum* blocking peptides, *P. falciparum* antisera, *P. falciparum* receptor agonists and *P. falciparum* receptor antagonists linked to cytotoxic agents. Such compositions are useful for research applications. The compositions, when combined with pharmaceutically acceptable excipients, or sustained-release compounds or compositions, such as biodegradable polymers, are useful as therapeutic agents such as vaccine or treatment compositions.

Diagnostic and analytical methods and kits may be developed for detection and measurement of *P. falciparum* in a variety of biological samples including biological fluids and biological tissues, and for localization of *P. falciparum* in tissues and cells. The method and kit can be in any configuration well known to those of ordinary skill in the art.

The methods of the present invention include methods of treating, diagnosing and preventing *P. falciparum* diseases such as malaria. Also provided are methods of detecting EBA-175 protein, *P. falciparum* and *P. falciparum* erythrocyte binding proteins. These methods employ the EBA-175 antibodies and peptides described herein. Methods of prevention may include passive immunization prior to infection by *P. falciparum* parasites to inhibit parasitic infection of erythrocytes. Methods of treatment may also include administration after infection to inhibit the spread of the parasite and ameliorate the symptoms of *P. falciparum* infection. Methods of diagnosis of *P. falciparum* infection include methods directed toward combining a biological sample with the antibodies described herein, wherein the binding of the antibodies indicates malaria. Methods of detection of *P. falciparum* and *P. falciparum* erythrocyte binding proteins include methods directed toward the detection of EBA-175 protein, *P. falciparum* and *P. falciparum* erythrocyte binding proteins in biological samples such as biological fluids and tissues and in culture media.

Accordingly, it is an object of the present invention to provide compositions comprising one or more EBA-175 antibodies or blocking peptides.

It is another object of the present invention to provide a method for the treatment of *P. falciparum* related diseases such as malaria.

It is a further object of the present invention to provide a method for the treatment of malaria, wherein compositions comprising one or more EBA-175 antibodies and/or blocking peptides are administered to an individual in need of such treatment.

It is another object of the present invention to provide a method for the diagnosis of *P. falciparum* related diseases such as malaria.

It is yet another object of the present invention to provide a method for the diagnosis of malaria, wherein compositions comprising one or more EBA-175 antibodies are used.

A further object of the present invention is to provide a method for the prevention of *P. falciparum* related diseases such as malaria.

It is another object of the present invention to provide a method for the prevention of malaria, wherein compositions comprising one or more EBA-175 antibodies or peptides are administered to an individual in need of such prevention.

Another object of the present invention to provide a method of detection of *P. falciparum* in culture media and in biological samples such as biological tissues and fluids.

It is a further object of the present invention to provide a method of detection of *P. falciparum*, wherein compositions comprising one or more EBA-175 antibodies are used.

These and other objects, features and advantages of the present invention will become apparent after a review of the following detailed description of the disclosed embodiments and the appended claims.

BRIEF DESCRIPTION OF THE FIGURES

Region I of EBA-175 encompasses amino acid residues 20–157, region II amino acids 145–760, region III–V amino acids 743–1322 and region VI amino acids 1304–1394. Region II is further subdivided into regions F1 and F2.

Following panning against a constrained heptapeptide M13 phage display library using EBA-175 antibody R256, the amino acid sequence of several peptides was determined. Six of eleven peptides contained the sequence of PEP R256-2, while one of the peptides contained the sequence of PEP R256-1.

FIG. 3: Percentage of *P. falciparum* growth inhibition by EBA-175 Monoclonal Antibodies Monoclonal antibodies R215, R216, R217 and R256 were tested for their ability to neutralize merozoite invasion in vitro. As compared to control monoclonal antibodies, R215, R217 and R256 blocked 82%, 83% and 76%, respectively, of merozoite invasion in the homologous FVO strain. Additionally, R215, R217 and R256, blocked 35%, 39% and 37%, respectively, of merozoite invasion in the heterologous 3D7 strain.

DETAILED DESCRIPTION

Compositions and methods for treating *P. falciparum* infection, diagnosing diseases related to *P. falciparum* infection, and preventing diseases related to *P. falciparum* infection are provided. The compositions are isolated antibodies and peptides that inhibit binding of *P. falciparum* erythrocyte binding proteins and fragments thereof. The antibodies and peptides of the present invention bind to an EBA-175 erythrocyte binding protein of a *Plasmodium* species. In one embodiment of the present invention, the *Plasmodium* species is *P. falciparum* and the EBA-175 protein is that as described in Camus and Hadley (1985), Sim et di. (1990), and Orlandi et al. (1992).

As used herein, the terms "antibody" and "antibodies" include monoclonal antibodies, polyclonal, chimeric, single chain, bispecific, simianized, and humanized antibodies, Fab fragments, including the products of an Fab immunoglobulin expression library, and peptide antibody fragments. Also as used herein, the terms "EBA-175 antibody" or "EBA-175 antibodies" refer to antibodies that bind to an EBA-175 erythrocyte binding protein of a *Plasmodium* species. It is also to be understood that as used herein, the term "isolated" refers to a composition which is substantially or essentially free from at least some of the components that normally accompany it in its native state. Thus, the isolated EBA-175 antibodies and proteins of this invention do not contain some of the materials normally associated with their in situ environment. Typically, the isolated EBA-175 antibodies and proteins of the invention are at least about 80% pure, usually at least about 90% pure, and preferably at least about 95% pure as measured by band intensity on a silver stained gel.

It is to be understood that the term "isolated" does not exclude fusion proteins comprising the EBA-175 antibodies and proteins from the present invention. The present invention contemplates fusion proteins, or chimeric proteins, comprising the EBA-175 antibodies and proteins described herein and other proteins. The present invention also includes humanized EBA-175 antibodies. For example, EBA-175 antibodies described herein that are of murine origin may be humanized by methods known to those of skill in the art.

Examples of methods used to humanize antibodies of non-human origin are the use of transgenic mice having genes encoding human immunoglobulins and the use of recombinant technology to create a fusion protein comprising the variable region domains of the non-human antibodies and human immunoglobulin genes. Therefore, the present invention contemplates humanized EBA-175 antibodies comprising the variable regions of the antibodies described herein and the non-variable regions of human immunoglobulin, and in particular, human IgG.

Additionally, the terms "a", "an" and "the" as used herein are defined to mean "one or more" and include the plural unless the context is inappropriate. The terms "polypeptide", "peptide", and "protein", as used herein, are interchangeable and are defined to mean a biomolecule composed of two or more amino acids linked by a peptide bond.

The present invention includes antibodies and peptides that specifically bind to an EBA-175 erythrocyte binding protein of a *Plasmodium* species. As used herein, the terms "specifically bind" and "selectively bind" are synonymous and refer to a binding reaction in which, under designated immunoassay conditions, the specified antibodies and peptides bind preferentially to a particular peptide/protein or antibody, respectively, and do not bind in a significant amount to other peptides/proteins or antibodies present in the sample. The specific binding is determinative of the presence of a peptide or antibody in the presence of a heterogeneous population of proteins and other biologics. Specific binding to a peptide or antibody under such conditions requires an antibody or blocking peptide that is selected for its specificity for a particular protein. A variety of immunoassay formats may be used to select antibodies and peptides specifically immunoreactive with a particular protein. For example, solid-phase ELISA immunoassays are routinely used to select monoclonal antibodies specifically immunoreactive with a protein. See, Harlow and Lane (1988) *Antibodies, A Laboratory Manual*, Cold Spring Harbor Publications, New York, for a description of immunoassay formats and conditions that can be used to determine specific immunoreactivity.

Figure 1:
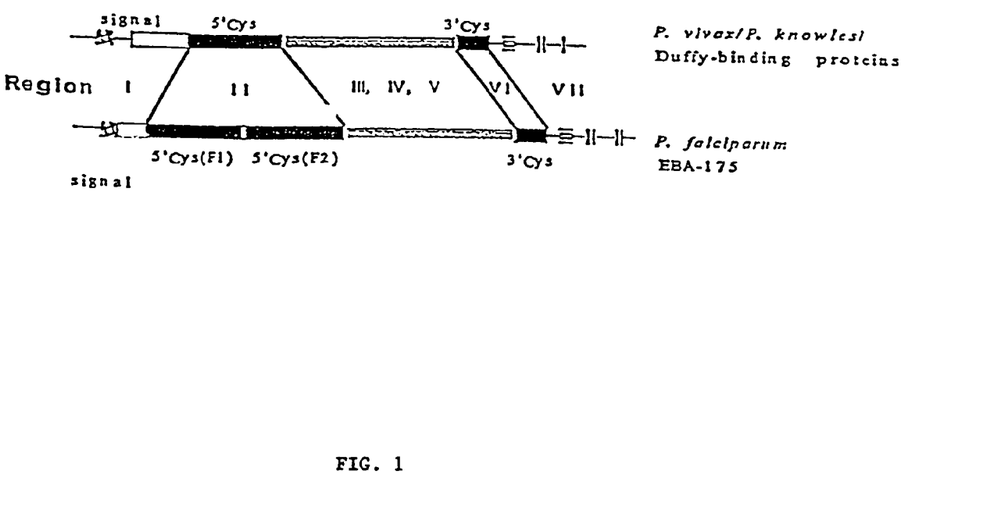
FIG. 1: Gene Structure of *P. Erythrocyte* Binding Proteins

In one embodiment of the present invention, an antibody binds to a 5' cysteine rich region of an EBA-175 erythrocyte binding protein of a *Plasmodium* species. In a preferred embodiment, the *Plasmodium* species is *P. falciparum*. The 5' cysteine rich region of *P. falciparum* is shown in FIG. 1 as Region II. Region II encompasses approximately amino acids 145–760 of the EBA-175 protein. As shown in FIG. 1, the 5' cysteine rich region is further divided into two regions F1 and F2 that are designated herein as RII/F1 and RII/F2, respectively. Included in the present invention are antibodies that bind to Region II of an EBA-175 protein of *P. falciparum*, and more preferably bind to the RII/F2 region of an EBA-175 protein of *P. falciparum*.

In one embodiment of the present invention, an antibody is provided that binds to a region of an EBA-175 protein, wherein the region consists of an approximately 10 amino acid sequence that is a fragment of an RII/FII region of an EBA-175 protein. In a further embodiment, the 10 amino acid sequence corresponds to approximately amino acids 488–497 of an EBA-175 protein, and more preferably has the amino acid sequence of CVPPRRQELC (SEQ ID NO:1).

The compositions of the present invention also include peptides that inhibit binding of a *Plasmodium* species and/or EBA-175 proteins or peptides to erythrocytes. As used herein, the term "EBA-175 peptide" refers to a 5–100 amino acid sequence of an EBA-175 protein of a *Plasmodium* species, more preferably a 5–25 amino acid sequence of an EBA-175 protein of a *Plasmodium* species, and most preferably a 5–15 amino acid sequence of an EBA-175 protein of a *Plasmodium* species. In one embodiment, the peptides inhibit binding of the erythrocyte binding protein EBA-175 as defined by Camus and Hadley (1985), Sim et al. (1990), and Orlandi et al. (1992). In another embodiment, the present invention provides an EBA-175 peptide that corresponds to approximately amino acids 488–497 of an EBA-175 protein. In a preferred embodiment, the peptides have the amino acid sequences of CVPPRRQELC (SEQ ID NO:1), CNMVPMSRC (SEQ ID NO:2) or CWSINPRWC (SEQ ID NO:3). When creating the peptides of the present invention, it is to be noted that the peptides may optionally comprise a carboxy-terminal amino acid sequence of GGGS (SEQ ID NO:4) as is well known in phage display techniques.

The terms "corresponding to" and "corresponds to", when referring to amino acids, indicates the comparison of two amino acids in the same region of different proteins, or fragments thereof, wherein the proteins are homologs, orthologs or paralogs. Homologs are defined as proteins with substantial homology, wherein "substantial homology" is defined below. Orthologs are defined as proteins having non-identical amino acid sequences and similar functional characteristics, wherein the proteins are from different species, but wherein the species have a common ancestral origin. Paralogs are defined as proteins having non-identical amino acid sequences and similar functional characteristics, wherein the proteins are from the same species.

It is also to be understood that the present invention is contemplated to include any EBA-175 peptide derivative. An EBA-175 peptide derivative includes a protein having an amino acid sequence of an EBA-175 peptide. An EBA-175 peptide derivative also includes a peptide having a sequence corresponding to an EBA-175 peptide subsequence. A "subsequence" is a sequence of contiguous amino acids found within a larger sequence. As defined herein, a larger sequence is an EBA-175 peptide of approximately 10 amino acids. A subsequence is generally composed of approximately at least 70%, more preferably 80%, and most preferably 90% of the larger sequence.

An EBA-175 peptide derivative also includes a peptide having a modified sequence in which one or more amino acids in the original sequence or subsequence have been substituted with a naturally occurring amino acid residue or amino acid residue analog (also referred to as modified amino acid). Suitable EBA-175 peptide derivatives have modified sequences which are substantially homologous to the amino acid sequence of an EBA-175 peptide or to an antiangiogenic subsequence of a EBA-175 peptide.

An "amino acid residue" is a moiety found within a protein or peptide and is represented by —NH—CHR—CO—, wherein R is the side chain of a naturally occurring amino acid. When referring to a moiety found within a peptide, the terms "amino acid residue" and "amino acid" are used interchangeably. An "amino acid residue analog" includes D or L configurations having the following formula: —NH—CHR—CO—, wherein R is an aliphatic group, a substituted aliphatic aromatic group, a benzyl group, a substituted benzyl group, an aromatic group or a substituted aromatic group and wherein R does not correspond to the side chain of a naturally occurring amino acid.

Suitable substitutions for amino acid residues in the sequence of the EBA-175 peptides described herein include conservative substitutions that result in EBA-175 peptides that block *P. falciparum* or EBA-175 protein binding to erythrocytes. A conservative substitution is a substitution in which the substituting amino acid (naturally occurring or modified) is structurally related to the amino acid being substituted. "Structurally related" amino acids are approximately the same size and have the same or similar functional groups in the side chains.

Provided below are groups of naturally occurring and modified amino acids in which each amino acid in a group has similar electronic and steric properties. Thus, a conservative substitution can be made by substituting an amino acid with another amino acid from the same group. It is to be understood that these groups are non-limiting and that additional modified amino acids could be included in each group.

Group I includes leucine, isoleucine, valine, methionine and modified amino acids having the following side chains: ethyl, n-propyl n-butyl. Preferably, Group I includes leucine, isoleucine, valine and methionine.

Group II includes glycine, alanine, valine and a modified amino acid having an ethyl side chain. Preferably, Group II includes glycine and alanine.

Group III includes phenylalanine, phenylglycine, tyrosine, tryptophan, cyclohexylmethyl, and modified amino residues having substituted benzyl or phenyl side chains. Preferred substituents include one or more of the following: halogen, methyl, ethyl, nitro, —$NH_2$, methoxy, ethoxy and —CN. Preferably, Group III includes phenylalanine, tyrosine and tryptophan.

Group IV includes glutamic acid, aspartic acid, a substituted or unsubstituted aliphatic, aromatic or benzylic ester of glutamic or aspartic acid (e.g., methyl, ethyl, n-propyl iso-propyl, cyclohexyl, benzyl or substituted benzyl), glutamine, asparagine, —CO—NH-alkylated glutamine or asparagine (e.g., methyl, ethyl, n-propyl and iso-propyl) and modified amino acids having the side chain —$(CH_2)_3$—COOH, an ester thereof (substituted or unsubstituted aliphatic, aromatic or benzylic ester), an amide thereof and a substituted or unsubstituted N-alkylated amide thereof. Preferably, Group IV includes glutamic acid, aspartic acid, methyl aspartate, ethyl aspartate, benzyl aspartate and methyl glutamate, ethyl glutamate and benzyl glutamate, glutamine and asparagine.

Group V includes histidine, lysine, ornithine, arginine, N-nitroarginine, β-cycloarginine, γ-hydroxyarginine, N-amidinocitruline and 2-amino-4-guanidinobutanoic acid, homologs of lysine, homologs of arginine and homologs of ornithine. Preferably, Group V includes histidine, lysine, arginine and ornithine. A homolog of an amino acid includes from 1 to about 3 additional or subtracted methylene units in the side chain.

Group VI includes serine, threonine, cysteine and modified amino acids having C1–C5 straight or branched alkyl side chains substituted with —OH or —SH, for example, —$CH_2CH_2OH$, —$CH_2CH_2CH_2OH$ or —$CH_2CH_2OHCH_3$. Preferably, Group VI includes serine, cysteine or threonine.

In another aspect of the present invention, suitable substitutions for amino acid residues in the amino acid sequences described herein include "severe substitutions" that result in EBA-175 derivatives that block *P. falciparum* or EBA-175 protein binding to erythrocytes. Severe substitutions that result in EBA-175 derivatives that block *P. falciparum* or EBA-175 protein binding to erythrocytes are much more likely to be possible in positions that are not highly conserved than at positions that are highly conserved. In the present invention, severe substitutions are much less likely to be possible in the conserved cysteine amino acid residues. A "severe substitution" is a substitution in which the substituting amino acid (naturally occurring or modified) has significantly different size and/or electronic properties compared with the amino acid being substituted. For example, the side chain of the substituting amino acid can be significantly larger (or smaller) than the side chain of the amino acid being substituted and/or can have functional groups with significantly different electronic properties than the amino acid being substituted.

Examples of severe substitutions of this type include the substitution of phenylalanine or cyclohexylmethyl glycine for alanine, isoleucine for glycine, a D amino acid for the corresponding L amino acid or —NH—CH[(—$CH_2)_5$—COOH]—CO— for aspartic acid. Alternatively, a functional group may be added to the side chain, deleted from the side chain or exchanged with another functional group. Examples of severe substitutions of this type include adding an amine or hydroxyl, carboxylic acid to the aliphatic side chain of valine, leucine or isoleucine, exchanging the carboxylic acid in the side chain of aspartic acid or glutamic acid with an amine or deleting the amine group in the side chain of lysine or ornithine. In yet another alternative, the side chain of the substituting amino acid can have significantly different steric and electronic properties that the functional group of the amino acid being substituted. Examples of such modifications include tryptophan for glycine, lysine for aspartic acid and —$(CH_2)_4COOH$ for the side chain of serine. These examples are not meant to be limiting.

"Substantial homology" exists between two amino acid sequences when a sufficient number of amino acid residues at corresponding positions of each amino acid sequence are either identical or structurally related such that a protein or peptide having the first amino acid sequence and a protein or peptide having the second amino acid sequence exhibit similar biological activities. Generally, there is substantial sequence homology among the amino acid sequences when at least 30%, more preferably at least 40%, and most preferably at least 50%, of the amino acids in the first amino acid sequence are identical to or structurally related to the second amino acid sequence. Homology is often measured using sequence analysis software, e.g., BLASTIN or BLASTP. The default parameters for comparing the two sequences (e.g., "Blast"-ing two sequences against each other) by BLASTIN (for nucleotide sequences) are reward for match=1, penalty for mismatch=−2, open gap=5, and extension gap=2. When using BLASTP for protein sequences, the default parameters are reward for match=0, penalty for mismatch=0, open gap=11, and extension gap=1.

The EBA-175 antibodies and peptides described herein are useful for the production of vaccines and therapeutic compositions. As used herein, the term "vaccine" includes compositions comprising the EBA-175 antibodies, or fragments thereof, as described herein, used for passive immunization of individuals prior to or following infection by *P. falciparum*. The term "vaccine" also includes compositions comprising the EBA-175 peptides described herein, used for active immunization of individuals prior to infection by *P. falciparum*. Accordingly, the present invention includes antibodies that inhibit binding of an EBA-175 protein to a red blood cell or erythrocyte. Additionally included in the present invention are antibodies that inhibit *P. falciparum* invasion into a red blood cell. The antibodies inhibit *P. falciparum* invasion of a red blood cell in vitro and/or in vivo.

The EBA-175 antibodies and peptides of the present invention can be isolated from serum or synthesized by chemical or biological methods. For example, the EBA-175 antibodies and peptides can be isolated from cell culture, produced by recombinant gene expression or polypeptide synthesis, or derived by in vitro enzymatic catalysis of larger, encompassing polypeptides to yield EBA-175 antibodies or peptides. Recombinant techniques include gene amplification from DNA sources using amplification techniques such as the polymerase chain reaction (PCR), and gene amplification from RNA sources using amplification techniques such as reverse transcriptase/PCR. In one embodiment, the EBA-175 peptides are produced and analyzed via phage display technology. Phage vectors that may be used in phage display technology include, but are not limited to, λ, M13, MS2, Mu, P4, λgtII, and φX174.

The EBA-175 antibodies and peptides of the present invention may be labeled directly with a detectable label for detection or identification of *P. falciparum* or antibody thereto. As used herein, the terms "detecting" or "detection" refer to quantitatively or quantitatively determining the presence of the biomolecule under investigation. Labels for use in immunoassays are generally known to those skilled in the art and include enzymes, radioisotopes, and fluorescent, luminescent and chromogenic substances including colored particles such as colloidal gold and latex beads. Suitable immunoassays include enzyme-linked immunosorbent assays (ELISA) and radioimmunoassays.

Alternatively, the EBA-175 antibodies and peptides of the present invention may be labeled indirectly by reaction with labeled substances that have an affinity for immunoglobulin, such as protein A or G or second antibodies. When using secondary antibodies, a suitable immunoassay is an immunoblot or Western blot. Additionally, the antibody or blocking peptide may be conjugated with a second substance and detected with a labeled third substance having an affinity for the second substance conjugated to the antibody. For example, the antibody or blocking peptide may be conjugated to biotin and the antibody-biotin conjugate detected using labeled avidin or streptavidin. Similarly, the antibody or blocking peptide may be conjugated to a hapten and the antibody-hapten conjugate detected using labeled anti-hapten antibody. These and other methods of labeling antibodies and assay conjugates are well known to those skilled in the art.

When labeled with a detectable biomolecule or chemical, the EBA-175 antibodies and peptides described above are useful for purposes such as in vivo and in vitro diagnostics and laboratory research using the methods and assays described below. Various types of labels and methods of conjugating the labels to the polypeptides and antibodies are well known to those skilled in the art. Several specific labels are set forth below.

For example, the EBA-175 antibodies and peptides are conjugated to a radiolabel such as, but not restricted to, $^{32}P$, $^3H$, $^{14}C$, $^{35}S$, $^{125}I$, or $^{131}I$. Detection of a label can be by methods such as scintillation counting, gamma ray spectrometry or autoradiography. Bioluminescent labels, such as derivatives of firefly iuciferin, are also useful. The bioluminescent substance is covalently bound to the polypeptide or antibody by conventional methods, and the labeled antibody is detected when an enzyme, such as luciferase, catalyzes a reaction with ATP causing the bioluminescent molecule to emit photons of light. Fluorogens may also be used as labels. Examples of fluorogens include fluorescein and derivatives, phycoerythrin, allophycocyanin, phycocyanin, rhodamine, and Texas Red. The fluorogens are generally detected by a fluorescence detector.

The EBA-175 antibodies and peptides can alternatively be labeled with a chromogen to provide an enzyme or affinity label. For example, the antibody can be biotinylated so that it can be utilized in a biotin-avidin reaction, which may also be coupled to a label such as an enzyme or fluorogen. Alternatively, the antibody or peptide can be labeled with peroxidase, alkaline phosphatase or other enzymes giving a chromogenic or fluorogenic reaction upon addition of substrate. Additives such as 5-amino-2,3-dihydro-1,4-phthalazinedione (also known as Luminol™) (Sigma Chemical Company, St. Louis, Mo.) and rate enhancers such as p-hydroxybiphenyl (also known as p-phenylphenol) (Sigma Chemical Company, St. Louis, Mo.) can be used to amplify enzymes such as horseradish peroxidase through a luminescent reaction; and luminogeneic or fluorogenic dioxetane derivatives of enzyme substrates can also be used. Such labels can be detected using enzyme-linked immunoassays (ELISA) or by detecting a color change with the aid of a spectrophotometer. In addition, EBA-175 antibodies and peptides may be labeled with colloidal gold for use in immunoelectron microscopy in accordance with methods well known to those skilled in the art.

The EBA-175 antibodies and peptides described herein are particularly useful for the treatment, prevention, diagnosis and detection of *P. falciparum* infections. The EBA-175 antibodies and peptides of the present invention may be used for the treatment, prevention, diagnosis or prognosis of *P. falciparum* related diseases such as malaria. Methods of prevention include passive immunization with the antibodies of the present invention prior to infection by *P. falciparum* to inhibit parasitic infection of erythrocytes. Methods of prevention also include active immunization with the blocking peptides of the present invention prior to infection by *P. falciparum* to inhibit parasitic infection of erythrocytes. Methods of treatment include administration of tie antibodies and/or blocking peptides after infection to inhibit the spread of the parasite and ameliorate the symptoms of *P. falciparum* infection.

Therefore, the present invention includes a method of treating a *Plasmodium* species related disease comprising, administering to an individual an isolated EBA-175 antibody in an amount effective to treat the *Plasmodium* species related disease. In one embodiment, the *Plasmodium* species is *P. falciparum*. In a further embodiment, the *P. falciparum* related disease is malaria. Also included in the present invention are methods of inhibiting *P. falciparum* invasion into a red blood cell of an individual comprising, administering to the individual an isolated EBA-175 antibody in an amount effective to inhibit *P. falciparum* invasion into the red blood cell.

The antibodies and peptides of the present invention may also be used to detect or quantify *P. falciparum* in a biological sample or specimen or culture media, or used in diagnostic methods and kits, as described below. Results from these tests can be used to predict or diagnose the occurrence or recurrence of *P. falciparum* mediated diseases such as malaria. Antibodies to the *P. falciparum* erythrocytic binding proteins may also be used in production facilities or laboratories to isolate additional quantities of the *P. falci-*

*parum* erythrocytic binding proteins, such as by affinity chromatography, or for the development of peptide agonists or antagonists.

*P. falciparum* related diseases such as malaria are prevented or treated by administering to a patient suffering from a *P. falciparum* related disease, a pharmaceutical composition containing substantially purified EBA-175 antibodies, EBA-175 peptides, EBA-175 polypeptide agonists or antagonists, or EBA-175 polypeptide antisera. Additional prevention and treatment methods include administration of EBA-175 antibodies, EBA-175 peptides, EBA-175 polypeptide antisera, or EBA-175 receptor agonists and antagonists linked to cytotoxic or anti-parasitic agents.

The antibodies specific for EBA-175 may be administered to a patient to passively immunize the patient against *P. falciparum* infection, thereby reducing *P. falciparum* related diseases such as malaria. The blocking peptides that specifically inhibit binding of *P. falciparum* to a red blood cell may also be administered to a patient to actively immunize the patient against *P. falciparum* infection, thereby reducing *P. falciparum* related diseases such as malaria. Administration of the EBA-175 antibodies or EBA-175 peptides may occur prior to any signs of *P. falciparum* infection. Such an administration would be important in individuals in areas where *P. falciparum* is endemic, or to individuals planning to travel to endemic areas. Administration of the EBA-175 antibodies and peptides may also occur after signs of *P. falciparum* infection have surfaced in order to interrupt the life cycle of the *Plasmodium* parasite and inhibit the spread of the organism.

In a preferred embodiment, a vaccine for passive or active immunization against malaria is packaged in a single dosage for immunization by parenteral (i.e., intramuscular, intradermal or subcutaneous) administration. The vaccine is most preferably injected intramuscularly into the deltoid muscle. The vaccine is preferably combined with a pharmaceutically acceptable carrier to facilitate administration. The carrier is usually water or a buffered saline, with or without a preservative. The vaccine may be lyophilized for re-suspension at the time of administration or in solution.

The carrier to which the antibody or peptides may be conjugated may also be a polymeric delayed release system. Synthetic polymers are particularly useful in the formulation of a vaccine to effect the controlled release of antibody. Microencapsulation of the antibody or peptide will also give a controlled release. A number of factors contribute to the selection of a particular polymer for microencapsulation. The reproducibility of polymer synthesis and the microencapsulation process, the cost of the microencapsulation materials and process, the toxicological profile, the requirements for variable release kinetics and the physicochemical compatibility of the polymer and the antigens are all factors that must be considered. Examples of useful polymers are polycarbonates, polyesters, polyurethanes, polyorthoesters polyamides, poly (d,l-lactide-co-glycolide) (PLGA) and other biodegradable polymers.

The preferred dose for human administration of the pharmaceutical composition or vaccine is from 0.01 mg/kg to 10 mg/kg. Based on this range, equivalent dosages for heavier body weights can be determined. The dose should be adjusted to suit the individual to whom the composition is administered and will vary with age, weight and metabolism of the individual. The vaccine may additionally contain stabilizers such as thimerosal (ethyl(2-mercaptobenzoate-S) mercury sodium salt) (Sigma Chemical Company, St. Louis, Mo.) or physiologically acceptable preservatives.

The antibodies of the present invention may also be used for the detection of *P. falciparum* peptides in biological samples or culture media. There are many techniques known in the art for detecting a component such as a polypeptide in a mixture and/or measuring its amount. Immunoassays, which employ antibodies that bind specifically to the polypeptide of interest, are one of the better known measurement techniques. Classical methods involve reacting a sample containing the polypeptide with a known excess amount of antibody specific for the polypeptide, separating bound from free antibody, and determining the amount of one or the other. Often the antibody is labeled with a reporter group to aid in the determination of the amount of bound analyte as described above. The reporter group or "label" is commonly a fluorescent or radioactive group or an enzyme.

An immunoassay is performed for the detection of *P. falciparum* in a sample as follows:

A sample is collected or obtained using methods well known to those skilled in the art. The sample containing the *P. falciparum* polypeptides to be detected may be obtained from an culture media or any biological source. Examples of biological sources include blood serum, blood plasma, urine, spinal fluid, fermentation fluid, lymph fluid, tissue culture fluid and ascites fluid. The sample may be diluted, purified, concentrated, filtered, dissolved, suspended or otherwise manipulated prior to immunoassay to optimize the immunoassay results.

To detect *P. falciparum* polypeptides, the sample is incubated with one or more of the *P. falciparum* erythrocyte binding protein antibodies of the present invention. The antibody may be labeled or conjugated to a solid phase bead or particle as also described herein. The labeled antibody is then detected using methods well known to those skilled in the art. The term "detecting" or "detected" as used herein means using known techniques for detection of biologic molecules such as immunochemical or histological methods. Such methods include immunological techniques employing monoclonal or polyclonal antibodies to the peptides, such as enzyme linked immunosorbant assays, radioimmunoassay, chemiluminescent assays, or other types of assays involving antibodies known to those skilled in the art.

Current binding assay technology benefits from the diversity of detection systems developed that use enzyme-catalyzed chromogenic reactions, radionuclides, chemiluminescence, bioluminescence, fluorescence, fluorescence polarization and a variety of potentiometric and optical biosensor techniques.

Binding assays rely on the binding of analyte by analyte receptors to determine the concentrations of analyte in a sample. Analyte-receptor assays can be described as either competitive or non-competitive. Non-competitive assays generally utilize analyte receptors in substantial excess over the concentration of analyte to be determined in the assay. Sandwich assays are examples of non-competitive assays, that comprise one analyte receptor frequently bound to a solid phase and a second analyte receptor labeled to permit detection. The analyte first binds to the analyte receptor bound to a solid phase and the second labeled analyte receptor is then added to facilitate quantitation of the analyte. Bound analyte can easily be separated from unbound reagents, such as unbound labeled first analyte receptors, due to the use of an analyte receptor bound to a solid phase.

Competitive assays generally involve a sample suspected of containing analyte, an analyte-analogue conjugate, and the competition of these species for a limited number of binding sites provided by the analyte receptor. Competitive assays can be further described as being either homogeneous or heterogeneous. In homogeneous assays all of the reactants participating in the competition are mixed together and the quantity of analyte is determined by its effect on the extent of binding between analyte receptor and analyte-conjugate or analyte analogue-conjugate. The signal observed is modulated by the extent of this binding and can be related to the amount of analyte in the sample. U.S. Pat. No. 3,817,837 describes such a homogeneous, competitive assay in which the analyte analogue conjugate is a analyte analogue-enzyme conjugate and the analyte receptor, in this case an antibody, is capable of binding to either the analyte or the analyte analogue. The binding of the antibody to the analyte analogue-enzyme conjugate decreases the activity of the enzyme relative to the activity observed when the enzyme is in the unbound state. Due to competition between unbound analyte and analyte analogue-enzyme conjugate for analyte-receptor binding sites, as the analyte concentration increases the amount of unbound analyte analogue-enzyme conjugate increases and thereby increases the observed signal. The product of the enzyme reaction may then be measured kinetically using a spectrophotometer.

Heterogeneous, competitive assays require a separation of analyte analogue conjugate bound to analyte receptor from the free analyte analogue conjugate and measurements of either the bound or the free fractions. Separation of the bound from the free may be accomplished by removal of the analyte receptor and anything bound to it from the free analyte analogue conjugate by immobilization of the analyte receptor on a solid phase or precipitation. The amount of the analyte analogue conjugate in the bound or the free fraction can then be determined and related to the concentration of the analyte in the sample. Normally the bound fraction is in a convenient form, for example, on a solid phase, so that it can be washed, if necessary, to remove remaining unbound analyte analogue conjugate and the measurement of the bound analyte analogue conjugate or related products is facilitated. The free fraction is normally in a liquid form that is generally inconvenient for measurements. If multiple analytes are being determined in a single assay, the determination of the free fraction of analyte analogue conjugate for each analyte is made impossible if all are mixed in a single liquid unless the responses of the individual analyte analogue conjugates can be distinguished in some manner. However, detecting the free fraction of analyte analogue conjugate in assays that are visually interpreted is a distinct advantage because the density of the color developed in such assays is generally proportional to the analyte concentration over much of the range of analyte concentration.

In a preferred embodiment, the method for detecting and characterizing P. falciparum polypeptides comprises taking a sample from a protein production lot. A determination of the presence of the immunodominant polypeptides can then be made using assay techniques that are well known to those skilled in the art and include methods such as Western blot analysis, radioimmunoassssay and ELISA assays.

In a second preferred embodiment, the method for detecting P. falciparum polypeptides comprises talking biological samples; such as fluids and tissues, from a mammal for the diagnosis or prognosis of malaria. The sample is preferably obtained from the blood, cerebrospinal fluid, urine or tissues of a mammal, preferably a human or simian. A determination of the presence of the immunodominant polypeptides can then be made using assay techniques that are well known to those skilled in the art and include methods such as Western blot analysis, radioimmunoasssay and ELISA assays.

A kit for detecting the presence and quantity of P. falciparum peptides is also provided. The kit can be in any configuration well known to those of ordinary skill in the art and is useful performing one or more of the methods described herein for the detection of P. falciparum in biological samples or for the detection or monitoring of P. falciparum infection in a patient or carrier. The kits are convenient in that they supply many if not all of the essential reagents for conducting an assay for the detection of P. falciparum in a biological sample. The reagents may be premeasured and contained in a stable form in vessels or on a solid phase in or on which the assay may be performed, thereby minimizing the number of manipulations carried out by the individual conducting the assay. In addition, the assay may be performed simultaneously with a standard that is included with the kit, such as a predetermined amount of antigen or antibody, so that the results of the test can be validated or measured.

The kit preferably contains one or more P. falciparum erythrocyte binding protein antibodies that can be used for the detection of P. falciparum binding proteins in a sample. The kit can additionally contain the appropriate reagents for binding or hybridizing the antibodies to their respective P. falciparum binding molecules or ligands in the sample as described herein and reagents that aid in detecting the bound peptides. The kit may additionally contain equipment for safely obtaining the sample, a vessel for containing the reagents, a timing means, a buffer for diluting the sample, and a colorimeter, reflectometer, or standard against which a color change may be measured.

In a preferred embodiment, the reagents, including the antibody, are lyophilized, most preferably in a single vessel. Addition of aqueous sample to the vessel results in solubilization of the lyophilized reagents, causing them to react. Most preferably, the reagents are sequentially lyophilized in a single container, in accordance with methods well known to those skilled in the art that minimize reaction by the reagents prior to addition of the sample.

The assay kit includes but is not limited to reagents to be employed in the following techniques; competitive and noncompetitive assays, radioimmunoassay, bioluminescence and chemiluminescence assays, fluorometric assays, sandwich assays, immunoradiometric assays, dot blots, enzyme linked assays including immunoblots and ELISAs, and immunocytochemistry. Materials used in conjunction with these techniques include, but are not limited to, microtiter plates, antibody coated strips or dipsticks for rapid monitoring of urine or blood. For each kit, the range, sensitivity, precision, reliability, specificity and reproducibility of the assay are established. Intraassay and interassay variation is established at 20%, 50% and 80% points on the standard curves of displacement or activity.

In a further preferred embodiment, the assay kit uses immunoblot techniques and provides instructions, P. falciparum polypeptides, and P. falciparum erythrocyte binding protein antibodies conjugated to a detectable molecule. The kit is useful for the measurement of P. falciparum in biological fluids and tissue extracts of animals and humans with and without malaria, as well as in culture media.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Production of Monoclonal Antibodies that Bind EBA-175

Mouse monoclonal antibodies were produced by the protocol as described in Harlow and Lane (1988) *Antibodies, A Laboratory Manual*, Cold Spring Harbor Publications, New York. Briefly, Balb/c mice were immunized with a purified recombinant baculovirus EBA-175 region II protein as an immunogen. Immune mice were used as splenocyte donors for fusion with a syngeneic mouse fusion partner, Sp2/0-Ag14. Hybridomas were selected based on the following criteria:
1. EBA-175 subcellular apical localization patterns on parasitized erythrocytes as determined by immunofluorescence assays;
2. ELISA positivity against a recombinant baculovirus region II protein; and
3. Neutralization of native EBA-175 binding to human erythrocytes.

Hybridomas that were selected were cloned twice by limiting dilution and maintained at −180° C.

EXAMPLE 2

Characterization of Monoclonal Antibodies that Bind EBA-175

Four IgG1 monoclonal antibodies labeled R215, R216, R217 and R256 were analyzed for the ability to block the binding of [$^{35}$S]methionine labeled EBA-175 to erythrocytes. Monoclonal antibodies R215, R217 and R256 inhibited greater than 90% binding, while R216 inhibited approximately 30% binding. (Data not shown). An RII EBA-175 region peptide expressed in baculovirus and RII, RII/F1 and RII/F2 EBA-175 region peptides expressed in yeast were separated by SDS-PAGE and probed with labeled monoclonal antibodies R216 and R217. Both the R216 and R217 antibodies did not recognize the RII/F1 region, but specifically recognized the RII/F2 region of EBA-175. (Data not shown). The most effective neutralizing antibodies, R215, R217 and R256, recognize a secondary structural epitope within the 5' cysteine rich region designated RII/F2. (Data not shown). In contrast, monoclonal antibody R216 recognizes a linear epitope within the 5' cysteine rich region designated RII/F2. (Data not shown).

Figure 3:
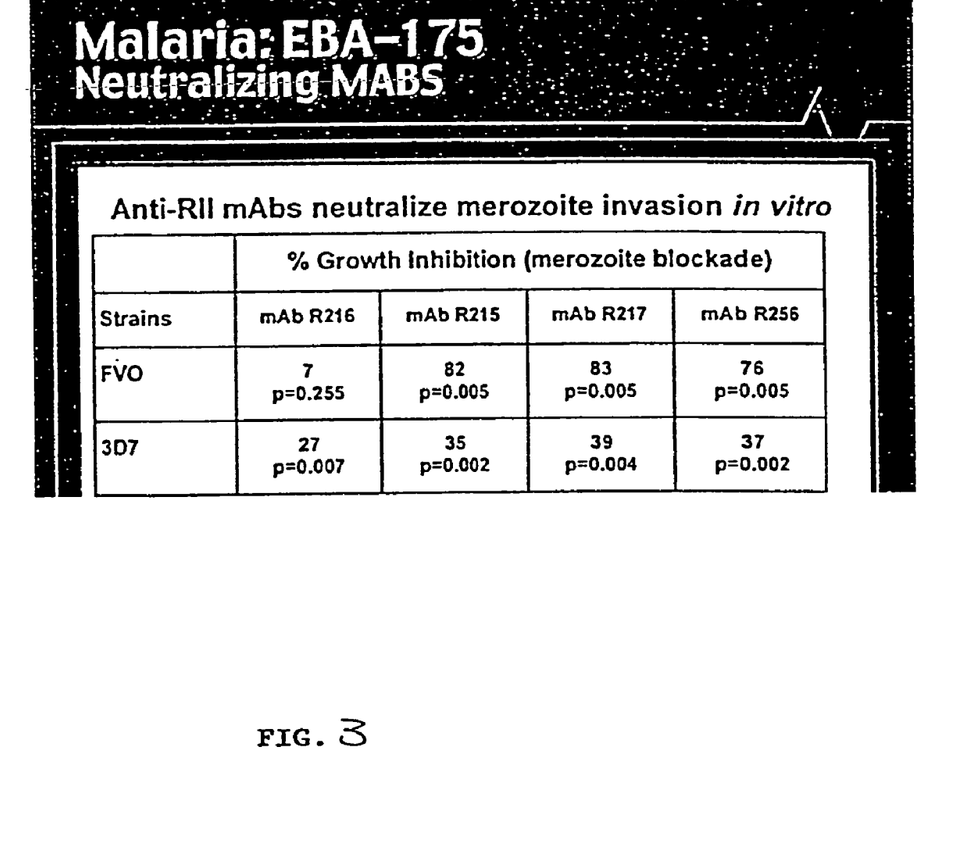

Additionally, monoclonal antibodies R215, R216, R217 and R256 were tested for their ability to neutralize merozoite invasion in vitro. As compared to control monoclonal antibodies, R215, R217 and R256 blocked 82%, 83% and 76%, respectively, of merozoite invasion in the homologous FVO strain. Additionally, R215, R217 and R256, blocked 35%, 39% and 37%, respectively, of merozoite invasion in the heterologous 3D7 strain. (See FIG. 3).

EXAMPLE 3

Amino Acid Sequence of EBA-175 Peptides

Figure 2:
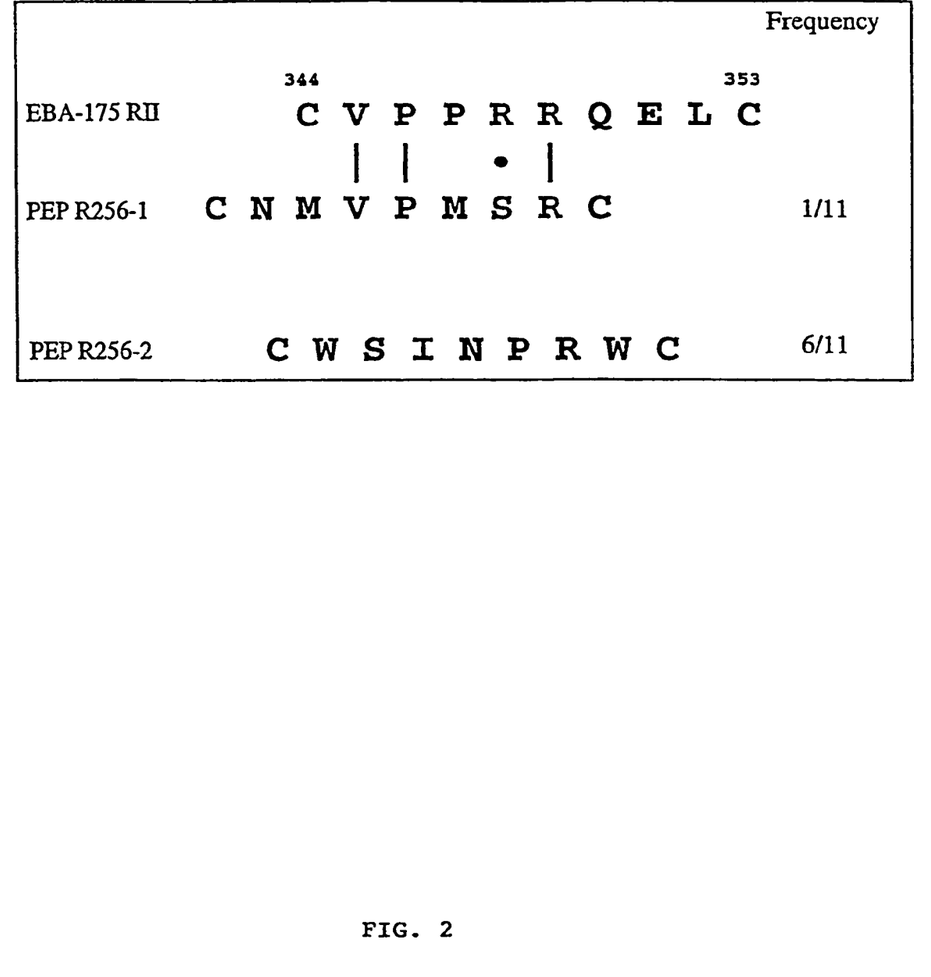
FIG. 2: Phage Sequence of two EBA-175 Blocking Peptides

Following panning against a constrained heptapeptide M13 phage display library using EBA-175 antibody R256, the amino acid sequence of several peptides was determined. Six of eleven peptides contained the sequence of PEP R256-2, while one of the peptides contained the sequence of PEP R256-1. (See FIG. 2).

Modifications and variations of the present method will be obvious to those skilled in the art from the foregoing detailed description. Such modifications and variations are intended to come within the scope of the appended claims.

REFERENCES

Camus, D. and T. J. Hadley. "A P. falciparum antigen that binds to host erythrocytes and merozoites." *Science*. 230 (4725): 553–6 (1985).

Chitnis, C. E. and L. H. Miller. "Identification of the erythrocyte binding domains of P. vivax and P. knowlesi proteins involved in erythrocyte invasion." *J Exp Med* 180(2): 497–506 (1994).

Hadley, T. J. "Invasion of erythrocytes by malaria parasites: a cellular and molecular overview." *Annu Rev Microbiol* 40: 451–77 (1986).

Sim, B. K., P. A. Orlandi, et al. "Primary structure of the 175K *P. falciparum* erythrocyte binding antigen and identification of a peptide which elicits antibodies that inhibit malaria merozoite invasion." *J Cell Biol* 111(5 Pt 1): 1877–84 (1990).

Fang, X., Kaslow, D. C., Adams, J. H., Miller, L. H. "Cloning of the P. vivax Duffy receptor." *Mol. Biochem. Parasitol.* 44: 125–132 (1991).

Adams, J. H., Hudson, D. E., Torii, M., Ward, G. E., Wellems, T. E., Aikawa, M., Miller, L. H. "The Duffy receptor family of P. knowlesi is located within the micronemes of invasive malaria merozoites." *Cell.* 63: 141–153 (1990).

Adams, J. H., Sim, B. K. L., Dolan, S. A., Fang, X., Kaslow, D. C., Miller, L. H. "A family of erythrocyte binding proteins of malaria parasites." *Proc. Natl. Acad. Sci.* 89: 7085–7089 (1992).

Orlandi, P. A., Klotz, F. W. and Haynes, J. D. "A malaria invasion receptor, the 175-kilodalton erythrocyte binding antigen of P. falciparum recognizes the terminal neu5Ac (α2–3)gal-sequences of glycophorin A." *J. Cell Biol.* 116: 901–909 (1992).

Sim, B. K. L., Chitnis, C. E., Wasniowska, K., Hadley, T. J., Miller, L. H. "Receptor and ligand domains for invasion of erythrocytes by *P. falciparum.*" *Science.* 264:1941–1944 (1994).

We claim:

1. An isolated antibody, wherein the antibody specifically binds a region of a RII/F2 region of an EBA-175 protein from a *Plasmodium* species, wherein the region consists of a 10 amino acid sequence and wherein the amino acid sequence is shown in SEQ ID NO: 1.

2. The isolated antibody of claim 1, wherein the P. species is *Plasmodium falciparum*.

3. The isolated antibody of claim 1, wherein the antibody inhibits binding of an EBA-175 protein to a red blood cell.

4. The isolated antibody of claim 1, wherein the antibody inhibits *Plasmodium falciparum* invasion into a red blood cell.

5. The isolated antibody of claim 4, wherein the antibody inhibits *Plasmodium falciparum* invasion of a red blood cell in vitro.

6. The isolated antibody of claim 4, wherein the antibody inhibits *Plasmodium falciparum* invasion of a red blood cell in vivo.

7. The isolated antibody of claim 1, wherein the antibody is monoclonal.

8. A hybridoma producing the monoclonal antibody of claim 7.

* * * * *

UNITED STATES PATENT AND TRADEMARK OFFICE
CERTIFICATE OF CORRECTION

PATENT NO. : 7,025,961 B1
APPLICATION NO. : 09/914694
DATED : April 11, 2006
INVENTOR(S) : Narum et al.

Page 1 of 1

It is certified that error appears in the above-identified patent and that said Letters Patent is hereby corrected as shown below:

On Title page and Col. 1, Line 1 In first page, Col. 1, title Item (54) delete "COMPOSITION" and insert -- COMPOSITIONS --.

Signed and Sealed this

Twentieth Day of March, 2007

JON W. DUDAS
*Director of the United States Patent and Trademark Office*